US009560938B2

(12) United States Patent
Dudda et al.

(10) Patent No.: US 9,560,938 B2
(45) Date of Patent: Feb. 7, 2017

(54) PAN LIFTING DEVICE

(71) Applicant: SARTORIUS LAB INSTRUMENTS GMBH & CO. KG, Goettingen (DE)

(72) Inventors: Olaf Dudda, Goettingen (DE); Wilfried Spannagel, Goettingen (DE); Caroline Schroeder, Goettingen (DE); Daniel Faerger, Goettingen (DE); Joerg Siedel, Goettingen (DE)

(73) Assignee: Sartorius Lab Instruments GmbH & Co. KG, Goettingen (DE)

( * ) Notice: Subject to any disclaimer, the term of this patent is extended or adjusted under 35 U.S.C. 154(b) by 0 days.

(21) Appl. No.: 15/185,530

(22) Filed: Jun. 17, 2016

(65) Prior Publication Data

US 2016/0287021 A1 Oct. 6, 2016

Related U.S. Application Data

(63) Continuation of application No. PCT/EP2014/003369, filed on Dec. 16, 2014.

(30) Foreign Application Priority Data

Dec. 17, 2013 (DE) .................. 10 2013 114 161

(51) Int. Cl.
*A47J 45/00* (2006.01)
*A47J 45/10* (2006.01)
*B25B 9/02* (2006.01)

(52) U.S. Cl.
CPC . *A47J 45/10* (2013.01); *B25B 9/02* (2013.01)

(58) Field of Classification Search
CPC ....................................................... A47J 45/10
USPC ...... 294/27.1, 29, 30, 31.1, 33, 34; 220/759; 16/425
See application file for complete search history.

(56) References Cited

U.S. PATENT DOCUMENTS

| 172,848 | A | * | 2/1876 | Conrade | ................. A47J 45/10 294/33 |
| 476,363 | A | * | 6/1892 | Traylor | .................... D06F 55/00 235/85 R |
| 784,803 | A | * | 3/1905 | Moylan | ................. B25J 15/0616 294/10 |
| 790,411 | A | * | 5/1905 | Watrous | ................. A47J 43/283 294/3 |

(Continued)

FOREIGN PATENT DOCUMENTS

DE  29615258 U1  10/1996
DE  3832726 C2   4/1997

(Continued)

OTHER PUBLICATIONS

International Search Report in counterpart International Application No. PCT/EP2014/003369, mailed Mar. 13, 2015.

(Continued)

*Primary Examiner* — Paul T Chin
(74) *Attorney, Agent, or Firm* — Edell, Shapiro & Finnan, LLC

(57) ABSTRACT

A pan lifting device configured to grip a pan of a balance with a positive fit has a pincer-shaped end (12) and a handle (14). A blade-shaped supporting projection (16) of the pan lifting device is configured to accommodate the bottom (28) of the pan and a bent-over beak (18) of the pan lifting device is configured to clamp the rim (30) of the pan.

11 Claims, 3 Drawing Sheets

(56) References Cited

U.S. PATENT DOCUMENTS

| | | | | |
|---|---|---|---|---|
| 850,737 | A | * | 4/1907 | Dellinger .................. A47J 45/10 294/29 |
| 865,917 | A | * | 9/1907 | Kuehnlein .............. A47J 45/10 294/29 |
| 1,538,536 | A | * | 5/1925 | Wisoff ................... A47J 43/283 294/177 |
| 1,541,738 | A | | 6/1925 | Peyton |
| 2,073,475 | A | * | 3/1937 | Gordon ................... A47J 45/10 220/759 |
| 2,228,547 | A | * | 1/1941 | Whitehead .............. A47J 45/10 294/34 |
| 2,333,564 | A | | 11/1943 | Hargrave |
| D149,920 | S | * | 6/1948 | Warner ........................ 294/99.2 |
| 2,595,683 | A | | 5/1952 | Monte |
| 5,787,600 | A | | 8/1998 | Leisinger et al. |
| 9,155,426 | B2 | * | 10/2015 | Corbin .................... A47J 45/10 |
| 2001/0039831 | A1 | | 11/2001 | Olesen |
| 2005/0001439 | A1 | | 1/2005 | Lukaszynski et al. |
| 2006/0208512 | A1 | * | 9/2006 | Romsburg, Sr. ......... A47J 45/10 294/31.1 |

FOREIGN PATENT DOCUMENTS

| | | |
|---|---|---|
| DE | 20210500 U1 | 11/2003 |
| DE | 202012102499 U1 | 8/2012 |
| EP | 1004859 B1 | 10/2004 |
| FR | 784609 A | 7/1935 |
| FR | 788517 A | 10/1935 |
| FR | 2406985 A1 | 5/1979 |

OTHER PUBLICATIONS

Office Action in corresponding German Application No. 10 2013 114 161.7, dated Oct. 9, 2014, along with an English translation.
International Preliminary Report on Patentability in counterpart International Application No. PCT/EP2014/003369, dated Nov. 17, 2015, along with a partial English translation.

* cited by examiner

PAN LIFTING DEVICE

CROSS REFERENCE TO RELATED APPLICATIONS

This is a Continuation of International Application PCT/EP2014/003369, which has an international filing date of Dec. 16, 2014, and the disclosure of which is incorporated in its entirety into the present Continuation by reference. The following disclosure is also based on and claims the benefit of and priority under 35 U.S.C. §119(a) to German Patent Application No. DE 10 2013 114 161.7, filed Dec. 17, 2013, which is also incorporated in its entirety into the present Continuation by reference.

FIELD OF THE INVENTION

The invention relates to a pan lifting device configured to grip a pan of a balance with a positive fit, wherein the pan has a bottom and an upwardly projecting peripheral rim.

The invention relates, in particular, to a pan lifting device configured to grip a disposable pan of a drying balance. In drying balances, the sample to be weighed is tested for its water content. Herein, the sample to be weighed is first weighed and subsequently subjected to a defined heat treatment.

BACKGROUND

A method for determining the water content using a drying balance is described in DE 38 32 726 C2.

EP 1 004 859 B1 discloses a drying balance wherein a cover is moved over the removable pan in order to close a weighing chamber. In order to remove the pan, the cover is moved back again into the housing of the drying balance. In this way, the accessibility of the pan is optimized.

However, there are also drying balances, i.e. above all, top-pan drying balances in which no movable cover is present, so that the weighing chamber is closed and is accessible via a hinged cover. Herein, the pan must be introduced into the weighing chamber laterally. As known, it is herein important that the pan is handled with a tool in order not to leave any contaminants on the pan.

A pan lifting device for gripping and conveying a pan is described in DE 202 10 500 U1. This pan lifting device is placed on the pan from above, wherein a handle extends vertically and has two limbs extending in opposing directions from its lower end. Mounted at the end of each of these limbs are U-shaped receptacles which, approaching from above, encompass the rim of the pan and extend as far as the bottom. Thus the pan is grasped from the diametrically opposite side in that the limbs press radially and against one another.

Forceps and pincers are known from U.S. Pat. No. 2,595,683 A, DE 20 2012 102 499 U1 and US 2005/0001439 A1 for entirely different purposes are not suitable for gripping a balance pan laterally, since on axial clamping, the pan would tilt in the forceps or pincers.

From U.S. Pat. No. 1,541,738 A, there is known a pincer-like kitchen lifting tool wherein two handle limbs are connected to one another via a hinge. A leaf spring presses the handle ends apart and thereby presses the gripping portions disposed before the hinge toward one another. A lower portion has a plate-shaped supporting projection. Using the universal pincers disclosed, it is intended that different pans can be lifted.

FR 784 609 A describes a clamping device for pans wherein, however, the upper handle and the lower handle transition into one another on the rear-side handle end. The lower grip limb has a plate-like projection which comes to lie under the pan, whereas the upper-side handle limb has a hook-shaped projection which, on pressing together the handle limbs, comes to lie against the inside of the pan.

Another pan lifter in the form of pincers is known from FR 788 517 A. This pan lifter is configured like a pair of shears or pincers, and formed onto the lower handle end is a plate-like projection which lies under the pan, and at the upper handle end an upwardly open U-shaped projection which is intended to grip the upper edge of the pan.

U.S. Pat. No. 2,333,564 A describes a pan lifter, the lower handle limb of which is configured as a planar part. With a pivot axis, an upper handle limb is pivotably articulated on the lower handle limb. In the region of the ends of the handle limbs, a compression spring which pre-tensions the pan lifter into a clamping position is arranged between the handle limbs. FR 2 406 985 A1 discloses a very similar pair of pincers.

SUMMARY

It is an object of the invention to provide a pan lifting device for a drying balance which enables easier handling of the pan, particularly in drying balances which have a hinged cover for opening the weighing chamber.

In drying balances of this type, a disadvantage of the known pan lifting device is that it requires much space during its use.

This and other objects are achieved with a pan lifting device wherein the pan lifting device has a pan-side pincer-shaped end and an oppositely-arranged handle, wherein the pincer-shaped end has a blade-shaped supporting projection which is configured to lie under the bottom of the pan, and has a beak which is configured to move toward and away from the supporting projection and is positioned over the supporting projection, is bent over and positively grips and clamps the rim of the pan. The supporting projection forms, in the direction opposed to the handle, the furthest forwardly projecting part of the pan lifting device. In the pan lifting device according to the invention, the two portions which engage with the pan are arranged one over the other and movable relative to one another. The supporting projection supports the bottom so that the bottom of the pan lies thereon. The beak, however, engages the rim portion of the pan lying thereabove and grips it so that the pan is clamped only in a narrow region and is thus removable laterally from the weighing chamber. Thus the operator does not have to reach into the weighing chamber with a hand, but can remove the pan from outside. The handle has two handle limbs which are movable relative to one another, specifically an upper limb and a lower limb. One handle limb is coupled to the supporting projection and the other handle limb is coupled to the beak, so that with a relative movement of the handle limbs, the supporting projection and the beak are moved relative to one another in order to open or close the pincer-shaped end.

The operation of the pan lifting device therefore takes place on the handle itself. The two handle limbs transition into one another to form a hinge or are coupled to one another there. In this manner, parts are spared and the pan lifting device can configured very easily and very simply. The upper handle limb is coupled to the supporting projection and the lower limb is coupled to the beak situated thereabove, so that seen in a side view, the handle limbs cross one another. The crossing site which is formed thereby is configured such that one handle limb has a through opening through which the other handle limb extends. The crossing site should be configured large enough so that a relative movement of the handle limbs is possible for opening and closing the pincer-shaped end.

Preferably, the handle is angled slightly upwardly relative to the supporting projection, but with the pan in use, extends substantially horizontally. This allows, as with a kitchen lifting device, the pan lifting device to be grasped and pushed under the pan.

In that the beak is movable relative to the supporting projection, with the pan lifting device opened, it is offset upwardly so that firstly the supporting projection is pushed under the pan. Subsequently, the beak engages on the rim, approaching from above, in order to clamp the pan.

One embodiment of the invention provides that the handle limbs transition into one another at the free handle end, in particular, forming a U-shape. Thus, the middle section of the "U" effectively forms the hinge.

The handle limbs can transition integrally into the supporting projection and into the beak, i.e. one handle limb transitions integrally into the supporting projection and the other into the beak. In this context, it can be advantageous if the handle limbs consist at least partially of plastics, so that the supporting projection and the beak are made of plastics. This allows gentle handling of the pan.

The handle limbs can be configured resilient relative to one another, i.e. a resiliently pre-tensioned starting position can be pre-determined and the handle limbs must then be moved against the spring force in order to open or close the pincer-shaped end.

A leaf spring which is connected to the handle limbs and which imparts the resilient effect can be integrated into the handle. Alternatively, the handle limbs can be configured as leaf springs in that a U-shaped or V-shaped leaf spring forms the two handle limbs with its limbs. In this embodiment, the supporting projection and the beak are then mounted on the respective leaf spring limbs, for example, by gluing, injection molding, screw fixing or other fastening types.

The preferred embodiment provides that the pan lifting device has no hinge with a separate axis, but that the mobility of the pan lifting device for opening and closing the pincer-shaped end is possible exclusively by elastic deformation of the pan lifting device.

The supporting projection tapers, for example, toward the free end, seen in plan view, and/or becomes continually thinner in its height, that is, in its vertical height toward the free end. These variants permit the supporting projection to be easily pushed under the pan base.

The supporting projection transitions on the handle-side end into an upwardly projecting shoulder. The beak has at least one downwardly projecting bent-over portion which is movable relative to the side surface of the shoulder which is associated with the pan rim and against which the pan rim lies. Thus, with the pincer-shaped end open, the beak extends upwardly so far that the supporting projection can be pushed under the bottom until the contacting of the pan rim against the shoulder without the beak causing an obstruction. Subsequently, the beak is moved downwardly. In this manner, the rim of the pan is laterally clamped between the bent-over portion or portions and the shoulder. The bent-over portion then lies against the inside of the pan rim and the outside of the pan rim is pressed against the shoulder, or more accurately stated, against the side surface of the shoulder.

BRIEF DESCRIPTION OF THE DRAWINGS

Further features and advantages of the invention are disclosed in the following description and the attached drawings, to which reference will be made. In the drawings.

DETAILED DESCRIPTION

Figure 1:
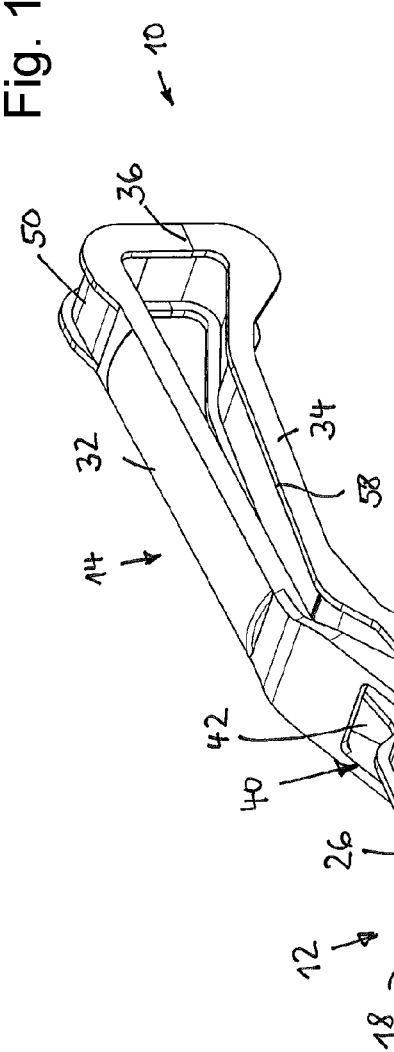
FIG. 1 is a perspective view of a first embodiment of the pan lifting device according to the invention.

FIG. 1 shows a pan lifting device 10 which serves for laterally inserting and removing a disposable pan in the weighing chamber of a drying balance.

The pan lifting device 10 comprises a plurality of sections, specifically a pan-side, pincer-shaped end 12 and a handle 14 opposite thereto.

The overall form of the pan lifting device is elongate, wherein in a side view (see FIG. 1), the handle 14 is bent-over upwardly somewhat in relation to the pincer-shaped end 12. In this way, the user can still reach with the fingers under the handle when the pincer-shaped end is already placed on a bottom of the drying balance or on a placement surface.

The pincer-shaped end 12 comprises two portions or parts movable toward and away from one another, specifically a blade-shaped supporting projection 16 and a slightly laterally offset beak 18, lying thereabove and extending less far forward.

The supporting projection 16 thus represents, in the opposite direction to the handle 14, the furthest forward projecting part of the pan lifting device.

Figure 2:
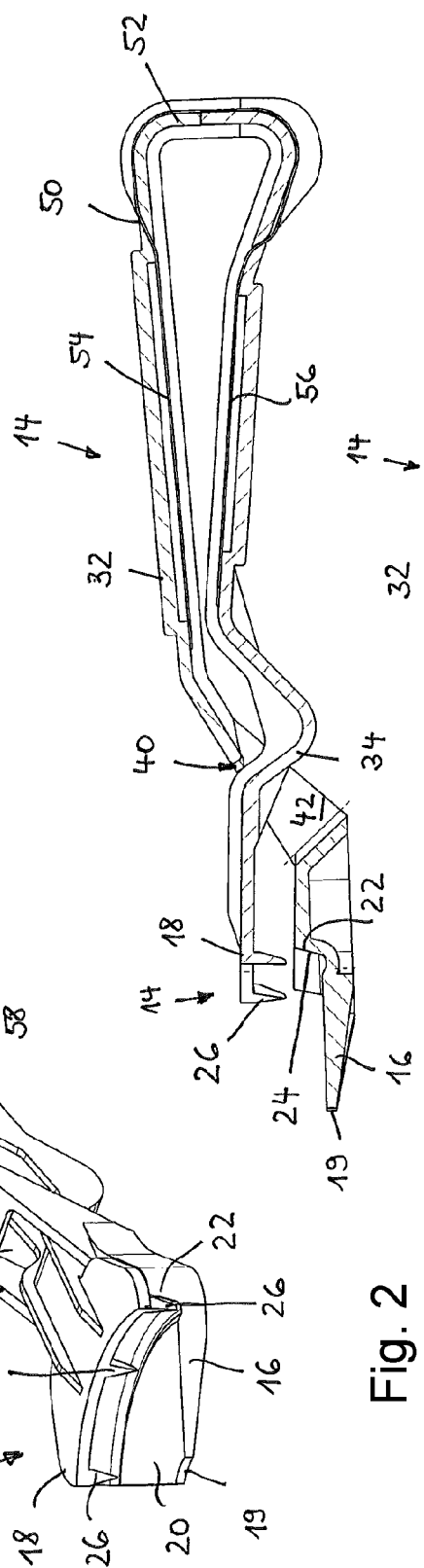
FIG. 2 is a longitudinal sectional view through the pan lifting device of FIG. 1 in the opened state.
Figure 3:
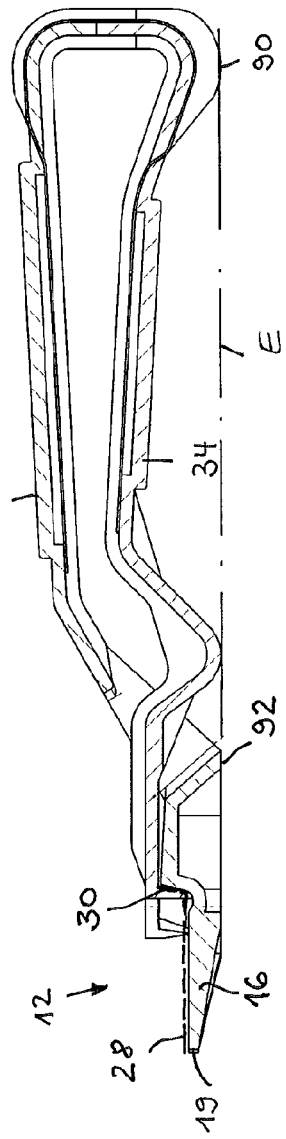
FIG. 3 is a longitudinal sectional view through the pan lifting device of FIG. 1 in the closed state.

As is clearly apparent in FIGS. 1 to 3, the supporting projection 16 tapers toward its free end 19, preferably conically.

Alternatively or additionally, the height or thickness of the supporting projection becomes ever less toward the free end 19, as is also clearly apparent from FIGS. 1 to 3.

The shell-shaped pan lies with its bottom 28 on the upper side 20 of the supporting projection.

The supporting projection 16 transitions into an upwardly projecting shoulder 22 or is delimited thereby, wherein the shoulder 22 has a side surface 24 facing toward the supporting projection 16, on which the outer rim 30 of the pan lies (see FIG. 3) on gripping the pan.

The beak 18 has at its front end, i.e. the end close to the supporting projection, a plurality of downwardly bent-over portions 26. Since the shoulder 22 has a circular segment form which corresponds to the circular form of the pan rim 30, the bent-over portions 26 also lie on the circular path, seen in plan view.

With the pincer-shaped end closed (see FIG. 3), the bent-over portions 26 lie against the side surface 24 or are spaced therefrom with a minimum gap so that the pan rim 30 is clamped between the side surface 24 and the opposite inner side of the bent-over portions 26.

The bent-over portions 26 are peripherally separated from one another and spaced so that point-type clamping sites are produced. This ensures the stable holding of the very thin pan.

In FIG. 3, a clamped pan is drawn in with dashed lines.

The supporting projection 16 and the beak 18 transition into the handle 14.

The handle 14 has two handle limbs extending toward one another, specifically an upper handle limb 32 and a lower hand limb 34.

The handle limbs 32, 34 are connected to one another at the free handle end. The line in FIG. 1 symbolizes the interface 36 of the two handle limbs 32, 34 manufactured as separate parts. In this region, the handle limbs 32, 34 are, for example, screwed to one another. The screw fixing itself is arranged on the rear side so that it is not visible in FIG. 1.

The handle limbs 32, 34 therefore form a U-shape wherein the central portion of the "U" forms a type of hinge 52 which is formed without an axis or an additional part.

The upper handle limb 32 transitions, as is to be understood herein as exemplary and not limiting, integrally into the supporting projection 16. The lower handle limb transitions, as is also to be understood herein as exemplary and not limiting, integrally into the beak 18. Since, therefore, the upper handle limb 32 is coupled to the supporting projection 16 arranged under the beak 18, the handle limbs 32, 34 cross one another, as shown in FIGS. 1 to 3. The result is a crossing site 40.

The crossing site 40 is configured in the embodiment shown in that the upper handle limb 32 has a, preferably elongate, through opening 42 through which the lower handle limb 34 extends.

The through opening 42 is configured as an elongate window and is thus peripherally closed in the embodiment shown.

Alternatively, the opening 42 can naturally also be configured as a laterally open cut-out, i.e. not configured as a closed window.

Furthermore, the through opening 42 can naturally also be conversely provided on the lower handle limb 34.

Integrated into the handle 14 is a spring, in this case a leaf spring 50, which presses the handle limbs 32, 34 away from one another. However, since the handle limbs 32, 34 joined to the supporting projection 16 and to the beak 18 cross one another, the leaf spring 50 has the effect that in the non-actuated starting position (rest position), the pincer-shaped end 12 is closed (FIG. 3).

In order to open the pincer-shaped end 12, the handle must be pressed together such that, with regard to FIGS. 2 and 3, the handle limbs 32, 34 are moved toward one another. Then the opened position is produced (FIG. 2).

The leaf spring 50 is configured U-shaped in the embodiment shown. At the U-shaped connecting portion (hinge 52) of the two handle limbs 32, 34, the leaf spring 50 extends externally. However, thereafter (see FIGS. 2 and 3), the two limbs 54, 56 extend along the inside, i.e. on sides of the handle limbs 32 or 34 facing one another and lie thereagainst.

The leaf spring 50 is laterally guided and held by projections 58 on the inside of the handle limbs 32, 34, so that no further, dedicated fasteners are needed.

The handle limbs 32, 34 and the supporting projection 16 and the beak 18 are made of plastics, particularly forming two plastics parts.

For assembly, the rear end of the lower handle limb 34 is pushed from the front through the through opening 42. Then, the handle limbs 32, 34 are connected to one another in the region of the interface 36. This connection can also be configured positively fitting without screw connections or other fasteners being needed. For example, a type of tongue and groove connection or a locking connection could be implemented.

If required, it is also possible for the pan lifting device 10 to be made without a leaf spring, so that the spring effect is realized purely through the two handle limbs 32, 34 without an additional part.

Figure 4:
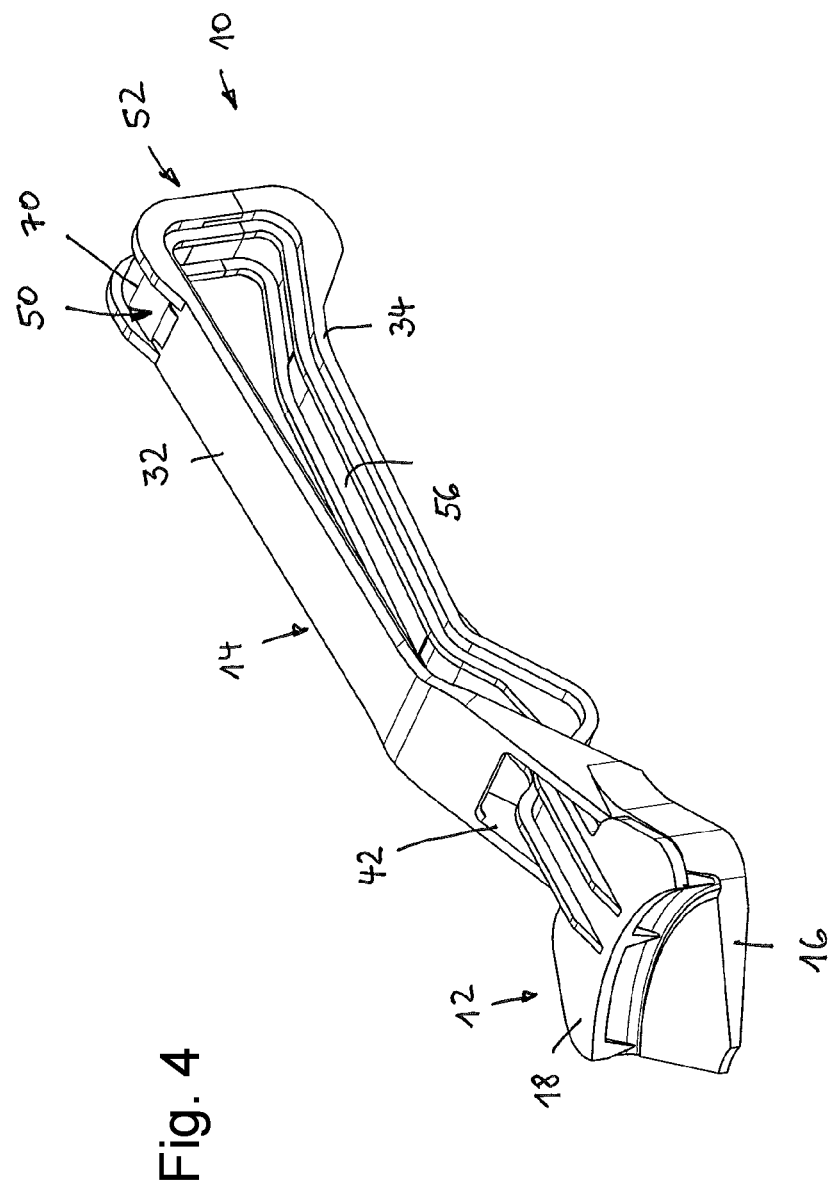
FIG. 4 is a perspective view of a second embodiment of the pan lifting device according to the invention.

The embodiment according to FIG. 4 corresponds to that of FIGS. 1 to 3 except for a few details, so that reference can be made to the entire content of the preceding embodiment, and the embodiment as per FIG. 4 can be regarded, with respect to any individual features, as analogous to that of FIGS. 1 to 3, except for the following differences.

In the embodiment of FIG. 4, the leaf spring 50 is configured somewhat differently.

Specifically, the leaf spring has a greater width in the region of the central section than in the region of the two limbs of the U. In the U-shaped region, the leaf spring 50 has the reference sign 70. The narrower portion (limb 56) which again lies on the inside is situated in the region of the limbs 32, 34. Here also, the leaf spring 50 extends on the outside in the region of the hinge 52 and otherwise on the inner sides of the handle limbs 32, 34 which face one another.

It is also possible, in general, thus not restricted to this embodiment, to injection mold at least one handle limb 32, 34 directly onto the leaf spring and to insert the other limb of the leaf spring 50 into the other handle limb 34 or 32 or, more generally, to fasten it thereto.

Figure 5:
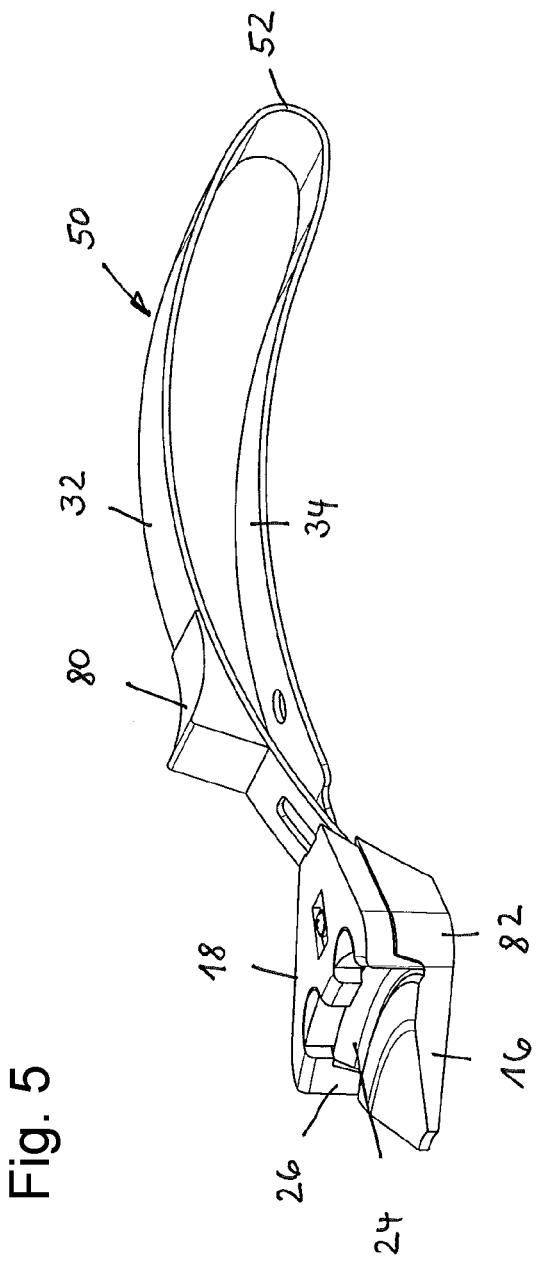
FIG. 5 is a perspective view of a third embodiment of the pan lifting device according to the invention.

Whereas in the previous embodiments, the handle limbs 32, 34 transition integrally into the associated portions of the pincer-shaped end 12 (supporting projection and beak), specifically integrally, in the embodiment of FIG. 5 it is provided that the handle 14 and the pincer-side end 12 consist of different parts.

The handle 14 is formed by the leaf spring 50 so that the leaf spring 50 also defines the handle limbs 32, 34 and the central portion of the U-shaped leaf spring 50 forms a hinge 52.

For better handling, although this should not be understood as restrictive, a plastics part 80 which facilitates handling can be mounted on the upper and/or lower handle limb 32, 34.

On the upper handle limb which crosses the lower handle limb 34, there is a part 82 mounted, for example by injection molding or screw fastening, clamping or the like, whereas the beak 18 is mounted on the lower handle limb, also by a screw fastening, clamping connection, locking connection or the like, or by injection molding on.

The part 82 then comprises the supporting projection 16 and the shoulder with the side surface 24.

In this embodiment, purely by way of example, two bent-over portions 26 are provided. Otherwise, the details of this embodiment also correspond to the embodiments above.

The underside 90 of the bent-over end of the handle lies in a plane E in which a, for example, planar portion of the underside 92 of the end 12 also lies, so that a stable placement surface results. In this manner, a pan lifting device 10 lies safely on a surface, even with a clamped pan.

LIST OF REFERENCE SIGNS

10 Pan lifting device
12 End
14 Handle
16 Supporting projection
18 Beak
19 End 20 Upper side
22 Shoulder
24 Side surface
26 Bent-over portion
28 Bottom
30 Pan rim
32 Handle limb
34 Handle limb
36 Interface
40 Crossing site
42 Through opening
50 Leaf spring
52 Hinge
54 Limb
56 Limb
58 Projections
70 U-shaped region
80 Plastics part
82 Part
90 Underside
92 Underside

What is claimed is:

1. A pan lifting device configured to grip a pan of a balance with a positive fit, wherein the pan has a bottom and an upwardly protruding peripheral rim, said pan lifting device comprising:
   a pan-side pincer-shaped end and an oppositely-arranged handle, wherein the pincer-shaped end has a blade-shaped supporting projection which is configured to lie under a bottom of the pan, and
   a beak which is bent-over and is configured to move toward and away from the supporting projection and is positioned over the supporting projection, so as to grip and clamp a rim of the pan, wherein:
      the supporting projection forms, in a direction opposed to the handle, a furthest forward projecting part of the pan lifting device,
      the handle comprises an upper handle limb and a lower handle limb, which are configured to move relative to one another,
      one of the handle limbs is coupled to the supporting projection and the other of the handle limbs is coupled to the beak, such that movement of the handle limbs relative to one another causes the supporting projection and the beak to move relative to one another, and thereby to open and close the pincer-shaped end,
      the two handle limbs transition into or are coupled to one another at the free handle end to form a hinge, and
      the upper handle limb is coupled to the supporting projection and the lower handle limb is coupled to the beak such that, when seen in a side view, the handle limbs cross one another at a site at which one of the handle limbs has a through opening, through which the other of the handle limbs extends.

2. The pan lifting device as claimed in claim 1, wherein the handle limbs transition into one another at the free handle end, forming a U-shape.

3. The pan lifting device as claimed in claim 1, wherein one of the handle limbs transitions integrally into the supporting projection and the other of the handle limbs transitions integrally into the beak.

4. The pan lifting device as claimed in claim 1, wherein the handle limbs are configured resilient in relation to one another.

5. The pan lifting device as claimed in claim 1, further comprising a leaf spring which is connected to both of the handle limbs and is integrated into the handle, or wherein the handle limbs are formed by a U-shaped leaf spring.

6. The pan lifting device as claimed in claim 1, wherein the handle limbs are each made of a plastics injection molded part and are coupled to one another at the grip end.

7. The pan lifting device as claimed in claim 1, wherein the supporting projection tapers toward the free handle end and/or becomes continually thinner toward the free handle end.

8. The pan lifting device as claimed in claim 1, wherein the supporting projection transitions at the handle-side end into an upwardly projecting shoulder and the beak has at least one downwardly projecting bent-over portion which is configured to move against the side surface of the shoulder.

9. The pan lifting device as claimed in claim 8, wherein, with the pan not clamped and not inserted, the at least one bent-over portion lies against the side surface.

10. The pan lifting device as claimed in claim 1, wherein, in the non-actuated state, the pan lifting device has a pre-determined rest position in which the pincer-shaped end is closed.

11. The pan lifting device as claimed in claim 1, wherein an underside of the downwardly bent-over end of the handle lies in a plane in which a portion of an underside of the pincer-shaped end also lies.

* * * * *